United States Patent
Liu et al.

(10) Patent No.: US 6,194,387 B1
(45) Date of Patent: Feb. 27, 2001

(54) 6-O-AKLYL ERYTHROMYCIN B OXIME

(75) Inventors: Jih-Hua Liu, Green Oaks; Stephen H. Montgomery, Vernon Hills, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/301,773

(22) Filed: Apr. 29, 1999

Related U.S. Application Data

(62) Division of application No. 08/980,918, filed on Dec. 1, 1997, now Pat. No. 5,932,710.

(51) Int. Cl.⁷ .............................. A61K 31/70; C07H 17/08
(52) U.S. Cl. .............................................. 514/29; 536/7.4
(58) Field of Search ........................ 536/7.2, 7.4; 514/29

(56) References Cited

U.S. PATENT DOCUMENTS

| | | | |
|---|---|---|---|
| 3,681,326 | 8/1972 | Von Esch et al. | 536/7.2 |
| 3,855,203 | 12/1974 | Hallas et al. | 536/7.2 |
| 4,496,717 | 1/1985 | Adachi et al. | 536/7.2 |
| 4,670,549 * | 6/1987 | Morimoto et al. | 536/7.4 |
| 4,672,109 | 6/1987 | Watanabe et al. | 536/7.2 |
| 4,680,386 * | 7/1987 | Morimoto et al. | 536/7.4 |
| 5,141,926 | 8/1992 | Weber et al. | 514/29 |
| 5,834,438 * | 11/1998 | Lartey et al. | 514/29 |

FOREIGN PATENT DOCUMENTS

| | | |
|---|---|---|
| 2350672 | 4/1974 | (DE) . |
| 0180415 | 5/1986 | (EP) . |

* cited by examiner

*Primary Examiner*—Elli Peselev
(74) *Attorney, Agent, or Firm*—Dugal S. Sickert

(57) ABSTRACT

A process of preparing a 6-O-alkyl derivative of 9-oxime erythromycin B is provided. Intermediates used in the preparation of a 6-O-alkyl 9-oxime erythromycin B are also provided. Pharmaceutical compositions containing a 6-O-alkyl derivative of 9-oxime erythromycin B and the use of those compositions to treat bacterial infections are also provided.

6 Claims, No Drawings

US 6,194,387 B1

6-O-AKLYL ERYTHROMYCIN B OXIME

This application is a divisional of U.S. patent application Ser. No. 08/980,918, filed Dec. 1, 1997, which issued as U.S. Pat. No. 5,932,710 on Aug. 3, 1999.

DESCRIPTION

1. Technical Field of the Invention

The present invention relates to erythromycin derivatives. More particularly, the present invention pertains to 6-O-alkyl derivatives of 9-oxime erythromycin B, a process for making those compounds and the use of the compounds as antibiotics.

2. Background of the Invention

Erythromycin B is a known macrolide antibiotic (C,E.G., U.S. Pat. No. 5,141,926) it is a fermentaion product produced by the gram-positive bacterium *saccharopolyspora erythraea*. Erythromycin B can be methylated at the 6-hydroxyl position to produce 6-O-methyl erythromycin B, the structure of which is shown below. There are no known reports, however, erythromycin B or 6-O-methyl of erythromycin B derivatives where in the keto group at position 9 has been replaced with alternative functional group.

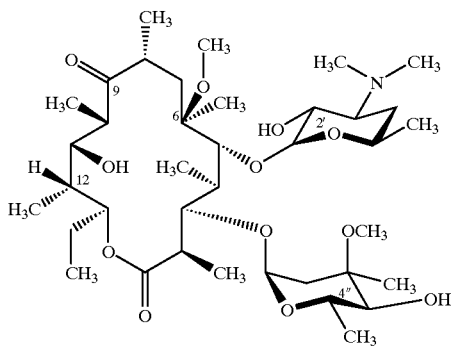

BRIEF SUMMARY OF THE INVENTION

The present invention provides 6-O-alkyl derivatives of 9-oxime erythromycin B and methods of synthesizing those compounds. A 6-O-alkyl derivative of 9-oxime erythromycin B compound of the present invention has the structure 1, below:

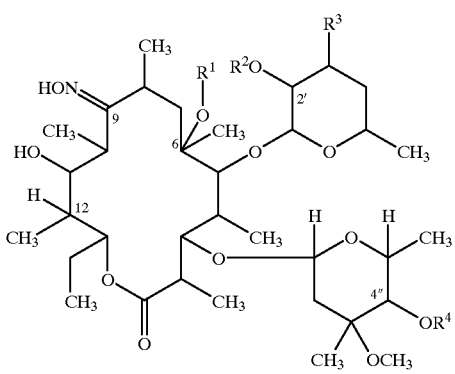

where $R^1$ is alkyl, $R^2$ and $R^4$ are each independently hydrogen or a conventional O-protecting group, and $R^3$ is $-NR^5(CH_3)_2$, where $R^5$ is methyl ($CH_3$) or a conventional N-protecting group or $-N^+(CH_3)_2R^6X^-$, where $R^6$ is 2-alkenyl, benzyl or substituted benzyl, and X is a halogen. In a preferred embodiment, $R^1$ is methyl, $R^2$ and $R^4$ are both hydrogen and $R^3$ is dimethylamine.

The synthetic process for making a 6-O-alkyl derivative of 9-oxime erythromycin B starts with conversion of erythromycin B (a fermentation product) to 2'-acetyl erythromycin B. That conversion is accomplished by reacting erythromycin B with an acetylating reagent such as acetic anhydride. 2'-Acetyl erythromycin B is then alkylated at the 6-hydroxyl to provide a 2'-acetyl-6-O-alkyl erythromycin B. Alkylation of the 6-hydroxyl group is accomplished using an alkylating reagent such as an alkyl halide or an alkyl sulfate. The 2'-acetyl-6-O-alkyl erythromycin B is then oximated and deacetylated to form 6-O-alkyl-9-oxime erythromycin B.

In another aspect, the present invention provides a pharmaceutical composition containing a 6-O-alkyl-9 derivative of oxime erythromycin B and a non-toxic pharmaceutically acceptable carrier. Still further, the present invention provides a method of treating a bacterial infection in a patient including the step of administering to the patient a therapeutically effective amount of a 6-O-alkyl derivative of 9-oxime erythromycin B. The compound of the invention is a useful intermediate in the synthesis of 6-O-methyl erythronolide B, disclosed in U.S. patent application Ser. No. 08/980,919 filed Dec. 1, 1997, now U.S. Pat. No. 5,919,916.

DETAILED DESCRIPTION OF THE INVENTION

A number of defined terms are used herein to designate particular elements of the present invention. When so used, the following meanings are intended:

The term "alkyl" refers to saturated, straight or branched-chain hydrocarbon radicals containing between one and ten carbon atoms including, but not limited to, methyl, ethyl, propyl, isopropyl, n-butyl, tert-butyl and neopentyl. More preferably, the alkyl is limited to 1-4 carbons.

The term "alkylating agent" refers to a reagent capable of placing an alkyl group onto a nucleophilic site, including, but not limited to, alkyl halides such as methyl bromide, ethyl bromide, n-propyl bromide, methyl iodide, ethyl iodide; and n-propyl bromide; dialkyl sulfates such as dimethyl sulfate, diethyl sulfate; and di-n-propyl sulfate; and alkyl or aryl sulfonates such as methyl-p-toluenesulfonate, ethyl methanesulfonate, n-propyl methanesulfonate, and the like.

The term "aryl(lower alkyl)" refers to a lower alkyl radical having appended thereto 1-3 aromatic hydrocarbon groups, as for example benzyl, diphenylbenzyl, trityl and phenylethyl.

The term "aryloxy" refers to an aromatic hydrocarbon radical which is joined to the rest of the molecule via an ether linkage (i.e., through an oxygen atom), as for example phenoxy.

The term "cycloalkyl" refers to a saturated monocyclic hydrocarbon radical having from three to eight carbon atoms in the ring and optionally substituted with between one and three additional radicals selected from among lower alkyl, halo(lower alkyl), lower alkoxy, and halogen. Examples of cycloalkyl radicals include, but are not limited to, cyclopropyl, cyclobutyl, cyclopentyl, cyclohexyl, cycloheptyl, 1-fluoro-cyclopropyl, and 2-fluorocyclopropyl.

The term "lower alkenyl" refers to a straight or branched-chain hydrocarbon radical containing between two and six carbon atoms and possessing at least one carbon-carbon double bond. Examples of lower alkenyl radicals include vinyl, allyl, 2- or 3-butenyl, 2-, 3- or 4-pentenyl, 2-, 4- or 5-hexenyl and isomeric forms thereof.

The term "lower alkoxy" refers to a lower alkyl radical which is joined to the rest of the molecule via an ether linkage (i.e., through an oxygen atom). Examples of lower alkoxy radicals include, but are not limited to, methoxy and ethoxy.

The term "lower alkyl" refers to an alkyl radical containing one to six carbon atoms including, but not limited to, methyl, ethyl, propyl, isopropyl, n-butyl, tert-butyl and neopentyl.

The term "polar aprotic solvent" refers to polar organic solvents lacking an easily removable proton, including, but not limited to, N,N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate, and the like.

The term "strong alkali metal base" refers to an alkali metal base having a weak conjugate acid, including, but not limited to, sodium hydroxide, potassium hydroxide, sodium hydride, potassium hydride, potassium t-butoxide, and the like.

The term "substituted aryl(lower alkyl)" refers to an aryl(lower alkyl) residue as defined above having between one and three non-hydrogen ring substituents, each independently selected from among halogen, lower alkoxy, lower alkyl, hydroxy-substituted lower alkyl, and (lower alkyl)amino. Examples of substituted aryl(lower alkyl) radicals include 2-fluorophenylmethyl, 4-fluorophenylethyl and 2,4-difluorophenylpropyl.

The term "weak organic amine base" refers to an organic amine base having a strong conjugate acid, including, but not limited to trimethylamine, triethylamine, tripropylamine, pyridine, 2-methoxypyridine, 1-methylpyrrolidine, 1-methylpiperidine, and 1-ethylpiperidine, and the like.

I. 6-O-Alkyl Derivatives of 9-Oxime Erythromycin B

A 6-O-alkyl derivative of 9-oxime erythromycin B has the structure I, below.

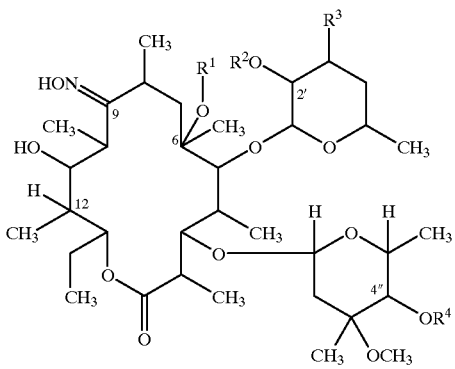

where $R^1$ is alkyl, $R^2$ and $R^4$ are each independently hydrogen or a conventional O-protecting group and $R^3$ is —$NR^5CH_3$, where $R^5$ is methyl ($CH_3$) or a conventional N-protecting group or —$N^+(CH_3)_2R^6X^-$, where $R^6$ is 2-alkenyl, benzyl or substituted benzyl, and X is a halogen. In a preferred embodiment, $R^1$ is methyl, $R^2$ is hydrogen or acetyl, $R^3$ is dimethylamine and $R^4$ is hydrogen.

The compound of structure I is shown without spatial bond orientation. Structure I thus defines all combinations of bond orientation and is intended to cover all possible stereo-configurations (e.g., epimers). In a preferred embodiment, the bond orientations of Structure I are the same as shown above for 6-O-methyl erythromycin B.

In structure I, the 2'- and/or 4"hydroxyl groups can contain conventional O-protecting groups that are well known in the art and include silyl, acyl, lower alkyl monocarbonyl, lower alkenyl monocarbonyl, alkoxycarbonyl, alkylcarbonyl, lower alkoxycarbonylalkylcarbonyl, and arylcarbonyl groups (See, e.g., Greene and Wuts' *Protective Groups in Organic Synthesis*, 2d. Ed. John Wiley & Sons, Inc., New York, 1991., the disclosure of which is incorporated herein by reference). Such a substituted erythromycin B oxime derivative results in a compound of structure I, where $R^2$ and $R^4$ are each independently silyl, carbonyl, acyl, alkoxycarbonyl, lower alkylcarbonyl, lower alkenyl monocarbonyl, lower alkoxycarbonylalkylcarbonyl, or arylcarbonyl. Exemplary and preferred lower alkyl monocarbonyl groups are acetyl, propionyl, butyryl, isobutyryl and the like. Acetyl is most preferred.

One of skill in the art will readily appreciate that it may be advantageous to also substitute for a methyl group of the dimethylamino moiety at the 3'-position of erythromycin A using a conventional N-protecting group. Exemplary and preferred N-protecting groups are alkoxycarbonyl groups (e.g., a methoxycarbonyl group, an ethoxycarbonyl group, an isopropoxycarbonyl group, an n-propoxycarbonyl group, an n-butoxycarbonyl group, an isobutyloxycarbonyl group, a sec-butyloxycarbonyl group, a t-butyloxycarbonyl group, a 2-ethylhexyloxycarbonyl group, a cyclohexyloxycarbonyl group, a methyloxycarbonyl group and the like); alkoxy-alkoxycarbonyl groups (e.g., a methoxymethoxycarbonyl group, an ethoxymethoxycarbonyl group, a 2-methoxyethoxy carbonyl group, a 2-ethoxyethylcarbonyl group, a 2-ethoxyethoxycarbonyl group, a 2-butoxyethoxycarbonyl group, a 2-methoxyethoxymethoxycarbonyl group and the like); haloalkoxycarbonyl groups (e.g., a 2-chloroethoxycarbonyl group, a 2-chloroethoxy carbonyl group, a 2,2,2-trichloroethoxycarbonyl group and the like), unsaturated alkoxycarbonyl groups (e.g., an allyloxycarbonyl group, a propargyloxycarbonyl group, a 2-butenoxycarbonyl group, a 3-methyl-2-butenoxycarbonyl group and the like), substituted benzyloxycarbonyl groups (e.g., a benzyloxycarbonyl group, a p-methylbenzyloxycarbonyl group, a p-methoxybenzyloxycarbonyl group, a p-nitrobenzyloxycarbonyl group, a 2,4-dinitrobenzyloxycarbonyl group, a 3,5-dimethylbenzyloxycarbonyl group, a p-chloro benzyloxycarbonyl group, a p-bromo benzyloxycarbonyl group and the like), and substituted phenoxycarbonyl groups [e.g., a phenoxycarbonyl group, a p-nitrophenoxycarbonyl group, an o-nitrophenoxycarbonyl group, a 2,4-dinitrophenoxycarbonyl group, a p-methyl phenoxycarbonyl group, an m-methyl phenoxycarbonyl group, an o-bromophenoxycarbonyl group, a 3,5-dimethylphenoxycarbonyl group, a p-chlorophenoxycarbonyl group, a 2-chloro-4-nitrophenoxycarbonyl group and the like (U.S. Pat. No. 4,672,109)].

The dimethylamino moiety at the 3'-position may also be protected as a quaternary salt by reacting with a 3'-dimethylamino derivative R—X, wherein R is a 2-alkenyl group, a benzyl group or a substituted benzyl group; and X is a halogen atom (See, e.g., U.S. Pat. No. 4,670,549). The 9-oximesilyl, 2'- and 4"-substituted erythromycin A derivative is then selectively alkylated at the 6-position. Procedures and reagents for alkylating the 6-position of erythromycin A derivatives are well known in the art (See, e.g., U.S. Pat. Nos. 4,672,109 and 4,670,549). In a preferred embodiment, $R^3$ is dimethylamino.

The present invention also provides pharmacologically acceptable salts, esters and prodrugs of 6-O-alkyl derivatives of 9-oxime erythromycin B. The term "pharmaceutically acceptable salts, esters, and prodrugs" as used herein refers to those carboxylate salts, esters, and prodrugs of the compounds of the present invention which are, within the scope of sound medical judgement, suitable for use in contact with the tissue of human and lower animals with undue toxicity, irritation, allergic response, and the like, commensurate with a reasonable benefit/risk ratio, and effective for their intended use, as well as the zwitterionic forms, where possible, of the compounds of the invention. Pharmaceutically acceptable salts are well known in the art and refer to the relatively non-toxic inorganic and organic acid addition salts of the compound of the present invention. For example, S. M. Berge, et al. Desribe pharmaceutically acceptable salts in detail in *J. Pharmaceutical Sciences*, 66: 1–19 (1977) which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with inorganic acids such as hydrochloric acid, hydrobromic acid, phosphoric acid, sulfuric acid and perchloric acid or with organic acid such as acetic acid, oxalic acid, maleic acid, tartaric acid, citric acid, succinic acid or malonic acid or by using other methods used in the art such as ion exchange. Other pharmaceutically acceptable salts indluce adipate, alginate, ascorbate, aspartate, benzenesulfonate, benzoate, bisulfate, borate, butyrate, camphorate, camphorsulfonate, citratre, cyclopentanepropionate, digluconate, dodecylsulfate, ethanesulfonate, formate, fumarate, gluocheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine actions formed using counterions such as halide, hydroxide, carboxylate, sulfate, phosphate, nitrate, loeralkyl sulfonate.

Example of pharmaceutically acceptable, non-toxic esters of the compounds of this invention include $C_1$ to $C_6$ alkanoyl esters wherein the alkanoyl group is a straight or branched chain. Esters of the compounds of the present invention may be prepared according to conventional methods.

The term "pharmaceutically acceptable prodrugs" as used herein refers to those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A through discussion is provided in T. Higuchi and V. Stella, *Pro-drugs as Novel Delivery Systems,* Vol. 14 of the A.C.S. Symposium Series, and in Edward B. Roche, ed., *Bioreversible Carriers in Drug Design,* American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxy-succinic acid amide ester method, cyanomethyl ester method and the like), the Woodward reagent K method, the DCC-HOBT (1-hydroxy-benzotriazole) method and the like. Classical methods for amino acid condensation reactions are described in M. Bodansky, Y. S. Klausner and M. A. Ondetti, *Peptide Synthesis,* Second Edirion, NY, 1976.

II. Preparation of 6-O-Alkyl Derivatives of 9-Oxime Erythromycin B

In another aspect, the present invention provides a process of preparing 6-O-alkyl derivatives of 9-oxime erythromycin B. In one embodiment, that process includes the steps of converting erythromycin B to a 2'-protected erythromycin B derivative, alkylating the 6-hydroxyl group, oximating the 9-keto group and deprotecting the 2'-hydroxyl group.

A process of the present invention begins with erythromycin B, typically produced using fermentation. As is well known in the art, to efficiently and selectively alkylate erythromycin B at the 6-OH position, the hydroxyl groups at the 2'- and/or 4"-positions should be protected prior to alkylation. It may also be desirable to protect the 3'-dimethylamino moiety. Such protection is accomplished by protecting those groups with conventional O- or N-protecting groups as set forth above. The use of O-protecting groups in the preparation of erythromycin derivatives has been described (See, e.g., U.S. Pat. No. 4,672,109, and European Patent Application 0260938A2, the disclosures of which are incorporated herein by reference). Conventional O-protecting groups, as set forth above, are positioned using standard procedures well known in the art.

A preferred O-protecting group is acetyl. An acetyl group can be positioned at the 2'-position by reacting erythromycin B with an acetylating agent in an aprotic solvent. Suitable acetylating agents that can be used include anhydride and acid halide compounds of the formula $(R^7CO)_2O$ or $R^7COCl$, where $R^7$ is hydrogen or a substituent group such as lower alkyl (e.g., methyl, ethyl, n-propyl, isopropyl, n-butyl, sec-butyl, t-butyl and the like) or aryl (e.g., phenyl, p-methoxyphenyl, p-chlorophenyl, m-chlorophenyl, o-chlorophenyl, 2,4,-dichlorophenyl, p-bromophenyl, m-nitrophenyl, p-nitrophenyl, benzhydryl, 1-naphthyl and the like). Examples of aprotic solvents are dichloromethane, chloroform, DMF, tetrahydrofuran, dimethyl sulfoxide, ethyl acetate and the like. The present invention provides that selective acetylation of the 2'-hydroxyl group can be accomplished by reacting the erythromycin B derivative with acetic anhydride in the presence of ethyl acetate. In accordance with this latter embodiment, erythromycin B is converted to 2'-acetyl erythromycin B.

The 3'-dimethyl group can optionally be protected with a conventional N-protecting group as set forth above. Means for N-protecting the 3'-dimethylamino group are well known in the art. In a preferred embodiment, however, it is not necessary to protect the 3'-dimethylamino group before selective alkylation of the 6-hydroxyl.

Alkylation of the 6-hydroxyl group is accomplished by reacting the 2'-protected erythromycin B derivative with an alkylating reagent in the presence of a suitable base. Exemplary and preferred alkylating agents are alkyl halides and alkyl sulfates such as methyl bromide, ethyl bromide, n-propyl bromide, methyl iodide, ethyl iodide, n-propyl bromide, dimethyl sulfate, diethyl sulfate, di-n-propyl sulfate, methyl-p-toluenesulfonate, ethyl methanesulfonate, and n-propyl methanesulfonate. In a preferred embodiment, the 6-hydroxyl group is methylated with a methylating reagent such as methyl bromide.

Exemplary and preferred bases are a strong alkali metal base, preferably selected from the group consisting of an alkali metal hydride, alkali metal hydroxide or alkali metal alkoxide, and a weak organic amine base, preferably selected from the group consisting of trimethylamine, triethylamine, tripropylamine, pyridine, 2-methoxypyridine, 1-methylpyrrolidine, 1-methylpiperidine, and 1-ethylpiperidine.

The alkylation step is carried out in a suitable solvent that includes methyl-t-butyl ether. Exemplary and preferred solvents are polar aprotic solvents such as N,N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate, or a mixture of such polar aprotic solvents maintained at a reaction temperature and for a period of time sufficient to effect alkylation, preferably from −15° C. to room temperature for a period of 1 to 8 hours.

Oximation is accomplished using standard procedures well known in the art. Briefly, the 2'-protected, 6-O-alkyl erythromycin B is reacted with either hydroxylamine hydrochloride and a base, free hydroxylamine in methanol or hydroxylamine and an organic acid (See, e.g., U.S. Pat. No. 5,274,085, the disclosure of which is incorporated herein by reference). Preferably, oximation is accomplished using hydroxyamine and formic acid in an alcohol solvent. It should be noted that, under these oximation conditions, the 2'-acetyl will be converted back to an hydroxyl. Thus, the oximation step provides the 6-O-alkyl 9-oxime erythromycin B without the need for any other additional steps. A detailed description of the synthesis of 6-O-methyl 9-oxime erythromycin B using a process of the present invention is set forth hereinafter in the Examples.

III. Pharmaceutical Compositions

In another aspect of the present invention, pharmaceutical compositions comprising a therapeutically effective amount of a compound of the present invention formulated together with one or more non-toxic pharmaceutically acceptable carriers are disclosed. As used herein, the term "pharmaceutically acceptable carrier" means a non-toxic, insert solid, semi-solid or liquid filler, diluent, encapsulating material or formulation auxiliary of any type. Some examples of materials which can serve as pharmaceutically acceptable carries are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phospate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils, (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral composition can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution. U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in preparation of injectables.

The injectables formulations can be sterilized, for example, by filtration through a bacterial-retaining filter, or by incorporating sterilizing agents in the form of sterile solid compositions that can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystlline or amorphous material with poor water solubility. The rate of absorption of the drug then depends upon its rate of dissolution which in turn, may depend upon crystal size and crystalline form. Alternatively, delayed absorption of a parenterally administered drug is accomplished by dissolving or suspending the drug in an oil vehicle. Injection depot forms are made by forming micorencapsule matrices of the drug in biodegradable polymers such as polylactide-polylactide-polyglycolide. Depending upon the ratio of drug to polymer and the nature of the particular polymer employed, the rate of drug release can be controlled. Examples of other biodegradable polymers include poly (orthoesters) and poly (anhydrides) Depot injectable formulations are also prepared by entrapping the drug in liposomes of microemulsions which are compatible with body tissues.

Compositions for rectal or vaginal administration are preferably suppositories which can be prepared by mixing the compounds of this invention with suitable non-irritating excipients or carries such as cocoa butter, polyethylene glycol or a suppository wax which are solid at ambient temperature but liquid at body temperature and therefore melt in the rectum or vaginal cavity and release the active compound.

Solid compositions of a similar type may be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings well known in the pharmaceutical formulating art. In such solid dosage forms, the active compound may be admixed with at least one inert diluent such as sucrose, lactose or starch. Such dosage forms may also comprise, as is normal practice, other inert diluents, e.g., tableting lubricants and other tableting acids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicaters and polyamide powder, or mixtures of these substances. Sprays can additionally contain customary propellants such as chlorofluorohydrocarbons.

Transdermal patches have the added advantages of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

IV. Method of Treating a Bacterial Infection

In a further aspect, the present invention provides a method of treating or preventing bacterial infections in a human or lower mammal comprising administering to a patient in need of such treatment or prophylaxis a therapeutically effective amount of a compound of the invention, for such time as is necessary to achieve a therapeutic effect. By a "therapeutically effective amount" of the compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physicians within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of the administration, and rate of excretion of the specific compound employed; the duration of the treatment; drugs used in combination or coincidental with the specific compound employed; and like factors well known in the medical arts.

The total daily dose of a compound of this invention administered to a human or other mammal in single or in divided dosages can be in amounts, for example, from 0.001 to 50 mg/kg body weight or more usually from 0.002 to 25 mg/kg body weight. Single dose compositions may contain such amounts or submultiples thereof to make up the daily dose. In general, treatment regimens according to the present invention comprise administration to a patient in need of such treatment from about 10 mg of the compound of this invention per day in multiple doses or in a single dose of from 10 mg to 1000 mg.

The Examples that follow illustrate preferred embodiments of the present invention and are not limiting of the specification and claims in any way.

EXAMPLE 1

Preparation of 2'-Acetyl Erythromycin B

Into a 1.0 L one neck round bottom flask were placed 50 g of erythromycin B (69.64 m mole), 500 mL ethyl acetate and 16 mL acetic anhydride (17.3 g, 169.6 m mole). The solution was stirred at room temperature overnight. Copious amounts of white solids were observed. This mixture was filtered to give 26.2 g solid. The filtrate was washed with 300 mL 5% sodium bicarbonate twice, and the organic layer was dried with magnesium sulfate. The solvent was removed by vacuum distillation to give a second crop of desired product (22.3 g). The product was identified by mass spectroscopy and NMR.

EXAMPLE 2

Preparation of 2'-Acetyl-6-O-Methyl Erythromycin B

Into a 1.0 L flask equipped with a thermometer, a stirrer, and a drying tube, were placed 137 mL tetrahydrofuran, 137 mL dimethyl sulfoxide and 23 g of 2'-acetyl erythromycin B (30.3 m mole). The solution was cooled with an ice bath to 0–5° C. and followed by addition of 6.2 g triethylamine, 7 mL of methyl bromide (12.11 g, 127.5 m mole) and 3.0 g powdered KOH (45.5 m mole). The temperature of the solution rose temporarily to 6° C. but returned to the cooling bath temperature soon thereafter. After 44 minutes the reaction quenched with 550 mL heptane and 110 mL 2N sodium hydroxide. The layers were separated and the organic phase was washed with 220 mL water, whereupon some solids appeared. The solids were filtered, 9.6 g and the filtrate concentrated to one-third volume under vacuum. More solids appeared and were filtered, 6.6 g; total amount:

16.2 g. The structure was confirmed by proton and C-13 NMR and mass spectroscopy.

EXAMPLE 3

Preparation of 6-O-Methyl Erythromycin B

To 600 mL of methanol, was added 8.4 g of 2'-acetyl-6-O-methyl erythromycin B (10.9 m mole). Into this solution and 300 mL of 5% potassium carbonate were added and the mixture stirred for three days. The volume of the resulting solution was reduced to 200 mL under vaccum. Solids were filtered and dried to give 7.37 g of the product.

EXAMPLE 4

Anti-Bacterial Activity of 6-O-Methyl 9-Oxime Erythromycin B

6-O-Methyl-9-oxime erythromycin B prepared in accordance with Examples 1 and 2 was assayed in vitro for anitbacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different micoorganisims, using a Steers replicatore block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as further control, as well as to provide test-to-test comparability. Erythromycin A was used for this purpose.

After incubation, each disk was read. The minimum inhibitory concentration (MIC) was defined as the lowest concentration of drug yielding no growth, a slight haze, or sparsely isolated colonies on the inoculum spot as compared to the growth control. The results of this assay, shown below in Tables 2 and 3, support the conclusion that 6-O-methyl-9-oxime erythromycin B is an effective antibacterial agent.

TABLE 2

| Organisims | Source | MIC ($\mu$g/ml) | SMIC (are disclosed $\mu$g/ml) |
|---|---|---|---|
| STAPHYLOCOCCUS AUREUS | ATCC 6538P | 0.39 | 0.39 |
| STAPHYLOCOCCUS AUREUS | A5177 | 6.2 | 12.5 |
| STAPHYLOCOCCUS AUREUS | A-5278 | >100 | >100 |
| STAPHYLOCOCCUS AUREUS | CMX 642A | 0.78 | 0.39 |
| STAPHYLOCOCCUS AUREUS | NCTC10649M | 0.39 | 0.39 |
| STAPHYLOCOCCUS AUREUS | CMX 553 | 0.78 | 0.39 |
| STAPHYLOCOCCUS AUREUS | 1775 | >100 | >100 |
| STAPHYLOCOCCUS EPIDERMIDIS | 3519 | 0.39 | 0.2 |
| ENTEROCOCCUS FAECIUM | ATCC 8043 | 0.1 | 0.05 |
| STAPHYLOCOCCUS BOVIS | A-5169 | 0.05 | 0.01 |
| STAPHYLOCOCCUS AGALACTIAE | CMX 508 | 0.05 | 0.01 |
| STAPHYLOCOCCUS PYOGENES | EES61 | 0.02 | 0.01 |
| STAPHYLOCOCCUS PYOGENES | 930 | >100 | >100 |
| STAPHYLOCOCCUS PYOGENES | PIU 2548 | 6.2 | 6.2 |
| MICROCOCCUS PYOGENES | ATCC 9341 | 0.05 | 0.01 |

TABLE 2-continued

| Organisims | Source | MIC ($\mu$g/ml) | SMIC (are disclosed $\mu$g/ml) |
|---|---|---|---|
| MICROCOCCUS LUTEUS | ATCC 4698 | 0.78 | 0.39 |
| ESCHERICHIA COLI | JUHL | 50 | 25 |
| ESCHERICHIA COLI | SS | 0.78 | 0.39 |
| ESCHERICHIA COLI | DC-2 | >100 | 100 |
| ESCHERICHIA COLI | H560 | 100 | 25 |
| ESCHERICHIA COLI | KNK 437 | 100 | 100 |
| ENTEROBACTER AEROGENES | ATCC 13048 | >100 | >100 |
| KLEBSIELLA PNEUMONIAE | ATCC 8045 | >100 | >100 |
| PROVIDENCIA STUART II | CMX 640 | >100 | >100 |
| PSEUDOMONAS AERUGINOSA | BMH10 | >100 | 100 |
| PSEUDOMONAS AERUGINOSA | 5007 | >100 | >100 |
| PSEUDOMONAS AERUGINOSA | K799/wt | >100 | >100 |
| PSEUDOMONAS AERUGINOSA | K799/61 | 1.56 | 0.78 |
| PSEUDOMONAS CEPACIA | 2961 | >100 | >100 |
| ACINETOBACTER CALCOACETICUS | CMX 669 | 50 | 12.5 |
| PSEUDOMONAS AERUGINOSA | DPHD-5263 | >100 | >100 |
| PSEUDOMONAS AERUGINOSA | DPHD-2862 | >100 | >100 |
| CANDIDA ALBICANS | CCH 442 | >100 | >100 |
| MYCOBACTERIIUM SMEGMATIS | ATCC 114 | 0.39 | 12.5 |
| NOCARDIA ASTEROIDES | ATCC 9970 | 0.1 | 0.005 |

TABLE 3

| Organisim | Source | MIC ($\mu$g/ml) | SIMC ($\mu$g/ml) |
|---|---|---|---|
| HAEMOPHILUS INFLUENZAE | CMX 503B | 16 | 8 |
| HAEMOPHILUS INFLUENZAE | CMX 504 | 16 | 8 |
| HAEMOPHILUS INFLUENZAE | CMX 519A | 16 | 4 |
| HAEMOPHILUS INFLUENZAE | CMX 566A | 16 | 4 |
| HAEMOPHILUS INFLUENZAE | CMX 588A | 16 | 4 |
| HAEMOPHILUS INFLUENZAE | CMX 632A | 8 | 4 |
| HAEMOPHILUS INFLUENZAE | CMX 747C | 16 | 8 |
| HAEMOPHILUS INFLUENZAE | CMX 751 | 32 | 8 |
| HAEMOPHILUS INFLUENZAE | DILL AMP R | — | — |
| HAEMOPHILUS INFLUENZAE | SPK AMP R | 16 | 4 |
| HAEMOPHILUS INFLUENZAE | SOL AMP R | 16 | 4 |
| HAEMOPHILUS INFLUENZAE | GYR 1177 | 1 | 0.25 |
| HAEMOPHILUS INFLUENZAE | GYR 1435 | 16 | 2 |
| HAEMOPHILUS INFLUENZAE | ATCC 10211 | 16 | 8 |
| HAEMOPHILUS INFLUENZAE | ATCC 19418 | 32 | 8 |
| HAEMOPHILUS INFLUENZAE | ATCC 43095 | 8 | 1 |
| STAPHYLOCOCCUS PYOGENES | EES61 | 0.03 | 0.03 |
| STAPHYLOCOCCUS PYOGENES | 930 | >128 | 128 |
| STAPHYLOCOCCUS PYOGENES | PIU 2548 | 16 | 16 |
| STAPHYLOCOCCUS PNEUMONIAE | ATCC 6303 | — | — |
| STAPHYLOCOCCUS PNEUMONIAE | GYR 1171 | 0.03 | 0.03 |
| STAPHYLOCOCCUS PNEUMONIAE | 5728 | >128 | 128 |
| STAPHYLOCOCCUS PNEUMONIAE | 5737 | >128 | 128 |
| STAPHYLOCOCCUS PNEUMONIAE | 5979 | >128 | 128 |
| STAPHYLOCOCCUS PNEUMONIAE | 5649 | 16 | 8 |
| STAPHYLOCOCCUS PNEUMONIAE | 5654 | 16 | 16 |

What is claimed is:
1. A compound of Structure I, below:

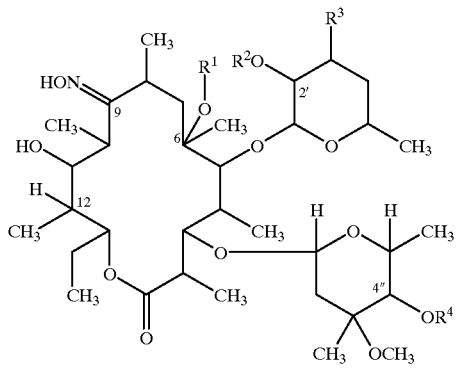

where $R^1$ is alkyl, $R^2$ and $R^4$ are each independently hydrogen, silyl, alkylcarbonyl, alkoxycarbonyl, acyl, lower alkenyl monocarbonyl, lower alkoxycarbonylalkylcarbonyl or arylcarbonyl; and $R^3$ is —$NR^5(CH_3)_2$, where $R^5$ is methyl or a N-protecting group or —$N^+(CH_3)_2R^6X^-$, where $R^6$ is 2-alkenyl, benzyl or substituted benzyl, and X is a halogen.

2. The compound of claim 1 wherein $R^1$ is methyl.

3. The compound of claim 2 wherein $R^2$ and $R^4$ are both hydrogen and $R^3$ is dimethylamino.

4. The compound of claim 1 wherein $R^1$ is methyl, $R^2$ is acetyl, $R^3$ is dimethylamino and $R^4$ is hydrogen.

5. A pharmaceutical composition comprising the compound of claim 1 and a pharmacologically acceptable carrier.

6. A process of treating a patient having a bacterial infection comprising administering to the patient a therapeutically effective amount of the compound of claim 1.

* * * * *